United States Patent [19]

Barth et al.

[11] Patent Number: 4,483,794
[45] Date of Patent: Nov. 20, 1984

[54] ANALOGS OF NEUROHYPOPHYSIAL HORMONES

[75] Inventors: Tomislav Barth, Roztoky u Prahy; Karel Jost, Prague 4; Michal Lebl, Prague 2; Alena Machová, Prague 9; Linda Servítová, Prague 4; Jirina Slaninová, Prague 1, all of Czechoslovakia

[73] Assignee: Ceskoslovenska akademie ved, Prague, Czechoslovakia

[21] Appl. No.: 493,370

[22] Filed: May 10, 1983

[51] Int. Cl.³ .................... C07C 103/52; H61K 37/00
[52] U.S. Cl. .............................. 260/112.5 R; 424/177
[58] Field of Search .................. 260/112.5 R; 424/177

[56] References Cited

U.S. PATENT DOCUMENTS

| 3,415,805 | 12/1968 | Siedel et al. | 260/112.5 R |
| 3,980,631 | 9/1976 | Prochazka et al. | 260/112.5 R |
| 4,237,119 | 12/1980 | Cort et al. | 260/112.5 R |
| 4,399,125 | 8/1983 | Manning et al. | 260/112.5 R |
| 4,402,942 | 9/1983 | Melin | 260/112.5 R |

OTHER PUBLICATIONS

Schroder, et al.; The Peptides (1966), pp. 320, 321, 324, 325, 334 & 335.

Primary Examiner—Delbert R. Phillips

[57] ABSTRACT

Analogs of neurohypophysial hormones with inhibition properties are described. The hormones are of the formula

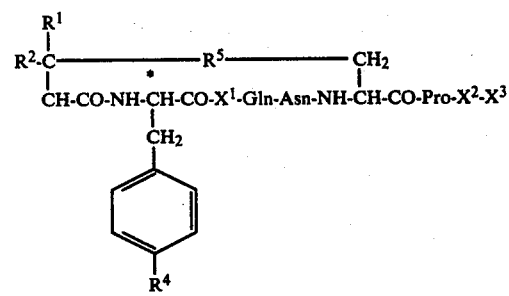

wherein in all chiral amino acids are of the L-series and the aromatic amino acid in the position 2, indicated with an asterisk, is of the D-series, and where $R^1$ and $R^2$ are hydrogen or a methyl group, $R^3$ is hydrogen, an amino group, or a triglycylamine grouping, $R^4$ is hydrogen, a methyl, ethyl or ethoxy group, $R^5$ is $S-CH_2$ or $S-S$ group, $X^1$ is a residue of isoleucine or phenylalanine, $X^2$ is a residue of leucine or lysine, and $X^3$ is a glycinamide residue or a hydroxyl group.

These compounds exhibit inhibition effects towards the uterotonic and pressor activity of natural hormones. The common structural feature of all these analogues is the presence of an aromatic hydrophobic D-amino acid in the position 2.

12 Claims, No Drawings

ANALOGS OF NEUROHYPOPHYSIAL HORMONES

This invention relates to analogs of neurohypophysial hormones, oxytocin and vasopressin which exhibit inhibitory effects toward the uterotonic and pressor activity of natural hormones. More particularly, the present invention relates to analogs of neurohypophysial hormones, oxytocin and vasopressin which share the common structural feature of an aromatic hydrophobic D-amino acid in the two (2) position to which is attributable the inhibitory effects of these analogs. Additional modifications of the structural nature of those analogs results in the enhancement of inhibitory effect.

It is well known that the neurohypophysial hormones possess several biological activities (Handbook of the Experimental Pharmacology, Vol. XXIII, Neurohypophysial Hormones and Similar Polypeptides, B. Berde, Ed.; Springer-Verlag, Berlin 1968) which are commonly utilized in the medical field. It is also known that compounds which negate (inhibit) certain of these biological activities are also useful.

In accordance with the present invention it has been determined that such compounds may conveniently be obtained by introducing an aromatic hydrophobic D-amino acid into the molecule of neurohypophysial hormones instead of in a tyrosine residue in the number two (2) position. When compared with the known analogs, the compounds described herein evidence a significant enhancement in inhibitory effect in combination with the ability to qualitatively modify the biological activity to yield a prolonged inhibitory effect (See Rudinger J., Krejci I. in Handbook of Experimental Pharmacology, Vol. XXIII. Neurohypophysial Hormones and Similar Polypeptides, B. Berde, Ed. pp. 748–801, Springer-Verlag, Berlin, 1968; Sawyer W. H., Grzonka Z., Manning M.: Mol. Cell. Endocrinol. 22, 117–134 (1981)).

The neurohypophysial hormones described herein are of the formula

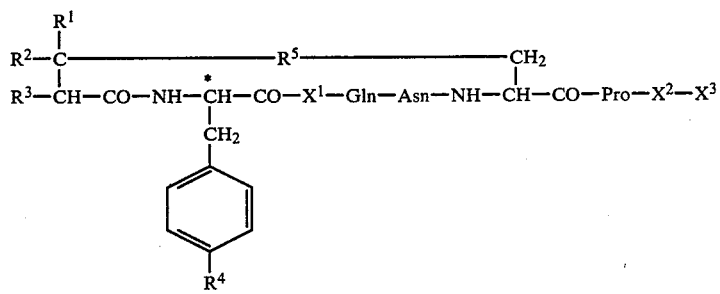

wherein chiral amino acids are of the L-series and the amino acids denoted by an asterisk are of the D-series. $R^1$ and $R^2$ being selected from among hydrogen and a methyl group, $R^3$ being selected from among hydrogen and a triglycylamino group. $R^4$ is selected from among hydrogen, methyl, ethyl and ethoxyl groups, $R^5$ is a $S-CH_2$ group or an $S-S$ group, $X^1$ is selected from among an isoleucine and phenylalanine residues, $X^2$ is selected from among a leucine and lysine residue and $X^3$ is selected from among a glycinamide residue and a hydroxyl group.

Compounds which are of particular interest herein are identified in the chart which follows:

| Compound | $R^1$ | $R^2$ | $R^3$ | $R^4$ | $R^5$ | $X^1$ | $X^2$ | $X^3$ |
|---|---|---|---|---|---|---|---|---|
| Ia | H | H | H | H | $S-CH_2$ | Ile | Leu | $GlyNH_2$ |
| Ib | H | H | H | $OC_2H_5$ | $S-CH_2$ | Ile | Leu | $GlyNH_2$ |
| Ic | H | H | H | $CH_3$ | $S-CH_2$ | Ile | Leu | $GlyNH_2$ |
| Id | H | H | H | $C_2H_5$ | $S-CH_2$ | Ile | Leu | $GlyNH_2$ |
| Ie | H | H | H | $C_2H_5$ | $S-S$ | Ile | Leu | $GlyNH_2$ |
| If | H | H | $NH_2$ | $C_2H_5$ | $S-S$ | Ile | Leu | $GlyNH_2$ |
| Ig | $CH_3$ | $CH_3$ | $NH_2$ | $C_2H_5$ | $S-S$ | Ile | Leu | $GlyNH_2$ |
| Ih | H | H | $NH_2$ | $C_2H_5$ | $S-S$ | Phe | Lys | $GlyNH_2$ |
| Ii | H | H | Gly—Gly—Gly—NH | $C_2H_5$ | $S-S$ | Ile | Leu | $GlyNH_2$ |
| Ij | H | H | H | $CH_3$ | $S-CH_2$ | Ile | Leu | OH |

Each of the above-identified analogs evidenced strong inhibitory effects. Table I, set forth below, set forth numerical values of the biological activity of these analogs wherein $pA_2$ represents the negative decadic logarithm of an inhibitory constant in accordance with the equation $$pA_2 = -\log \frac{B}{\frac{A_{50B}}{A_{50}} - 1}$$

wherein B is the concentration of the inhibitor in moles per liter, $A_{50}$ is the concentration of an agonistic compound (oxytocin) which results in 50% of the maximum effect, and $A_{50B}$ is the concentration of an agonistic compound yielding 50% of the maximum effect in the presence of an inhibitor of concentration B (Eggena P., Schwartz I. L., and Walter R.: J. Gen. Physiol. 52, 465 (1968).

TABLE I

| pA2 values as tested with an isolated rat uterus | |
|---|---|
| Compound | $pA_2$ |
| Ia | 8.26 |
| Ib | 7.54 |
| Ic | 8.73 |
| Id | 8.73 |
| Ie | 8.06 |
| If | 8.15 |
| Ig | 8.09 |
| Ih | 7.05(a) |
| Ii | 6.14(b) |

Formula I

TABLE I-continued pA$_2$ values as tested with an isolated rat uterus

| Compound | pA$_2$ |
|---|---|
| Ij | 8.8 |

[a] the negative decadic logarithm of the analog concentration which leads to suppression of the biological effect of vasopressin (i.e. of blood pressure in a despinalized rat) to 50% of the original response; the blood volume of rat (6.7 ml/100g of rat weight) is assumed in the in vivo test (Nestor J. J., Ferger M. F., du Vigneaud V.: J. Med. Chem. 18, 284 (1975)).

[b] the analog has a prolonged inhibitory effect toward the uterotonic activity of oxytocin in the in vivo test with a uterus as compared with the equipotential dose of the compound ([ 2-D-p-ethylphenylalanine] oxytocin).

The inhibitory effect of the described compounds is retained even when the glycinamide residue is removed from the molecule (compound Ij). It is understood that this type of replacement eliminates endocrine activities (Czechoslovakian Patent Applications PV 2803-82, PV 2099-81 and PV 8301-82) which is desirable from the standpoint of applying inhibitors. It was further determined that acylation of the primary α-amino group with a short peptide chain yielded an inhibitor with a prolonged effect. This effect is caused by a sequential enzymatic cleavage of the added portion of the molecule accompanied by the gradual generation of the inhibitor, that is, the use of the principle of hormonegen effect (Berankova-Ksandrova Z., Bisset G. W., Jost K., Krejci I., Pliska, V., Rudinger J., Rychlik I., Sorm F.: Brit. J. Pharmacol. 26, 615–632 (1966)) in the field of inhibitors.

The analogs described herein may be prepared in accordance with processes commonly used in the art for other purposes. the specific methodology for attaining this end will be more fully described in the exemplary embodiments which follow. It will be understood that these examples are solely for purposes of exposition and are not to be construed as limiting.

EXAMPLE 1

[2-D-Phenylalanine]deamino-6-carba-oxytocin 150 mg of O-nitrobenzenesulfenyl-D-phenylalanyl-isoleucyl-glutaminyl-asparaginyl-S-(β-carboxyethyl)-homocysteinyl-prolyl-leucyl-glycinamide was dissolved in 4 milliliters of dimethylformamide. Then, a solution of hydrogen chloride in ether (3.2M, 0.4 ml) was added, and the mixture allowed to stand for 6 minutes at ambient temperature. After the addition of ether, the hydrochloride of octapeptide precipitated, was reprecipitated from dimethylformamide with ether, filtered, and dried in vacuum. Then, it was dissolved in 4 milliliters of dimethylformamide, mixed with 181 mg of hydroxybenzotriazole, cooled to 0 degree C. and 200 mg of dicyclohexylcarbodiimide added thereto. The solution was next stirred for 1 hour at 0 degree C. and allowed to stand for 1.5 hours at ambient temperature. Then, separated crystals of urea were filtered off, the solution introduced into methanol (150 ml) heated to 45 degrees C. and the mixture adjusted to a pH of 8.5 by the addition of N-ethylpiperidine. The mixture was then heated to 45 degrees C. for 2 hours and concentrated to a small volume. The product was precipitated by addition of ether, filtered and dried in vacuum (140 mg). 30 mg of the product were dissolved in a mixture of methanol-water (1:1, 10 ml), applied on a column of silica gel modified with octadecyl chains (50×0.9 cm) and eluted with a mixture of methanol—0.05% aqueous trifluoroacetic acid (55:45). The fraction containing a compound of K=7.3 was concentrated in vacuum and freeze-dried yielding 6.5 mg of a compound, which was pure according to HPLC and TLC in four solvent systems. For $C_{44}H_{67}N_{11}O_{11}S \cdot 2H_2O$ (994.2) calculated: 53.16% C, 7.20% H, 15.50% N: found: 52.88% C, 7.39% H, 15.29% N. Analysis of amino acids: Asp 1.04, Glu 1.05, Pro 0.95, Gly 1.04, Ile 0.94, Leu 1.05, Phe 0.98, Hcy ($C_2H_4$COOH) 0.97.

EXAMPLE 2

[2-D-o-Ethyltyrosine]deamino-6-carba-oxytocin 130 mg of O-nitrobenzenesulfenyl-D-O-ethyltyrosyl-isoleucyl-glutaminyl-asparaginyl-S-(β-carboxyethyl)-homocysteinyl-prolyl-leucyl-glycinamide was cyclized in the same manner as set forth in Example 1. 135 mg of crude product was obtained and 30 mg was dissolved in the methanol-water (4:6), mixture applied on a column of silica gel modified with octadecyl chains (50×0.9 cm) and eluted with a methanol—0.05% aqueous trifluoroacetic acid (1:1) mixture. The fraction containing a compound of k=26.3 was concentrated and freeze-dried giving 6.2 mg of a pure compound according to HPLC and TLC. for $C_{46}H_{71}N_{11}O_{12}S \cdot 4H_2O$ (1074) calculated: 51.43% C, 7.41% H, 14.34% N; found: 51.27% C, 7.65% H, 14.08% N. Analysis of amino acids: Asp 1.02, Glu 1.03, Pro 1.00, Gly 1.04, Ile 0.93, Leu 0.98, Tyr (Et) 0.41, Tyr 0.56, Hcy($C_2H_4$COOH) 0.92.

EXAMPLE 3

[2-D-p-Methylphenylalanine]deamino-6-carba-oxytocin 220 mg of o-Nitrobenzenesulfenyl-D-p-methylphenylalanyl-isoleucyl-glutaminyl-asparaginyl-S-(β-carboxyethyl)homocysteinyl-prolyl-leucyl-glycinamide was cyclized in the same manner as set forth in Example 1. 30 mg of the crude product was purified in the manner of Example 1. The fraction containing a compound of k—13.6 was concentrated in vacuum and freeze-dried yielding 7.3 mg of a pure product according to HPLC and TLC. For $C_{45}H_{69}N_{11}O_{11}S \cdot 3H_2O$ (1026) calculated: 52.67% C, 7.37% H, 15.01% N; found 52.40% C, 7.61% H, 14.83% N.

Analysis of amino acids: Asp 1.00, Glu 1.00, Pro 1.05, Gly 1.01, Ile 0.91, Leu 1.04, Phe(Me) 0.99, Hcy($C_2H_4$COOH) 0.99.

EXAMPLE 4

[2-D-p-Ethylphenylalanine]deamino-6-carba-oxytocin 200 mg of o-Nitrobenzenesulfenyl-D-p-ethylphenylalanyl-isoleucyl-glutaminyl-asparaginyl-S-(β-carboxyethyl)homocysteinyl-prolyl-leucyl-glycinamide was cyclized and 30 mg of the product purified in the same manner as set forth in Example 1 yielding 5.3 mg of a pure compound according to HPLC and TLC. For $C_{46}H_{71}N_{11}O_{11}S \cdot 4H_2O$ (1055) calculated: 52.21% C, 7.52% H, 14.56% N; found: 51.90% C, 7.54% H, 14.41% N. Analysis of amino acids: Asp 1.01, Glu 1.03, Pro 0.94, Gly 0.99, Ile 0.92, Leu 1.05, Phe(Et) 1.00, Hcy($C_2H_4$COOH) 0.95.

EXAMPLE 5

[2-D-p-Ethylphenylalanine]deamino-oxytocin 50 mg of S-Benzylmercaptopropionyl-D-p-ethylphenylalanyl-isoleucyl-glutaminyl-asparaginyl-S-benzylcysteinyl-prolyl-leucyl-glycinamide was dissolved in liquid ammonia and reduced with a sodium rod until a stable blue coloration was obtained for 1 minute. The blue coloration was removed with a drop of acetic acid and the mixture freeze-dried. The lyophilizate was dissolved in 0.1M HCl (8 ml), diluted to 100 ml with water, and adjusted to a pH of 7 by the addition of 0.1M NaOH. Then, a solution of $K_3Fe(CN)_6$ (25 mg in 5 ml water) was added within 20 minutes while a pH of 7 was kept during this period. The mixture was then stirred for another 40 min at ambient temperature. Then, the pH was adjusted to 4 by the addition of acetic acid and the solution applied on a column with silica gel modified by octadecyl chains (25×0.4 cm) by means of a high-pressure pump. The column was washed with water and peptides were eluted with a methanol—0.05% aqueous trifluoroacetic acid (80:20) mixture. the eluate was concentrated in vacuum and freeze-dried, dissolved again in the methanol-water (1:1, 8 ml) mixture, applied on a column with silica gel modified with octadecyl chains (50×0.9 cm) and eluted with a methanol—0.05% aqueous trifluoroacetic acid (65:35) mixture. The fraction containing a compound of k=16.6 was concentrated in vacuum and freeze-dried yielding 8.6 mg of a product which was pure according to HPLC and TLC. For $C_{45}H_{69}N_{11}O_{11}S_2.4H_2O$ (1076) calculated: 50.22% C, 7.21% H, 14.32% N; found: 49.94% C, 7.24% H, 14.18% N. Analysis of amino acids: Asp 1.02, Glu 0.97, Pro 0.89, Gly 1.00, Cys 0.53, Ile 0.91, Leu 1.00, Phe(Et) 1.00.

EXAMPLE 6

[2-D-p-Ethylphenylalanine]oxytocin 200 mg of $N^\delta$-Benzyloxycarbonyl-S-benzylsteinyl-D-p-ethylphenylalanyl-isoleucyl-glutaminyl-asparaginyl-S-benzylcysteinyl-prolyl-leucyl-glycinamide was reduced and oxidized in the manner set forth in Example 5. After cyclization, the solution was applied on a column of carboxylic cation-exchanger (30 ml), the column washed with 0.25% acetic acid and peptides eluted with 50% acetic acid. One third of the product obtained by freeze-drying was dissolved in a methanol-water (1:1, 8 ml) mixture, applied on a column of silica gel modified with octadecyl chains (50×0.9 cm), and eluted with a methanol—0.1M aqueous ammonium acetate (60:40) mixture of pH 7. The fraction containing a compound of k=21.1 was concentrated in vacuum and freeze-dried yielding 16.3 mg of a product which was pure according to both HPLC and TLC. For $C_{45}H_{70}N_{12}O_{11}S_2.2H_2O.C_2H_4O_2$ (1115) calculated: 50.61% C, 7.05% H, 15.07% N; found: 50.36% C, 6.81% H, 15.23% N. Analysis of amino acids: Asp 0.96, Glu 0.98, Pro 1.02, Gly 0.96, Cys 1.73, Ile 1.06, Leu 1.03, Phe(Et) 1.02.

EXAMPLE 7

[1-Penicilamine, 2-D-p-ethylphenylalanine]oxytocin 200 mg of $N^\delta$-Benzyloxycarbonyl-S-benzyl-penicilaminyl-D-p-ethylphenylalanyl-isoleucyl-glutaminyl-asparaginyl-S-benzylcysteinyl-prolyl-leucyl-glycinamide was reduced and oxidized in the manner as set forth in Example 5. After cyclization the mixture was worked out and purified in the manner set forth in Example 6 with the exception that the mixture containing 65% methanol was used for elution. The pure product according to both HPLC and TLC was obtained in the amount of 8.2 mg. For $C_{47}H_{74}N_{12}O_{11}S_2.3H_2O.C_2H_4O_2$ (1161) calculated: 50.67% C, 7.29% H, 14.47% N; found: 50.78% C, 7.43% H, 14.31% N. Analysis of amino acids: Asp 0.98, Glu 1.00, Pro 0.89, Gly 1.00, Ile 1.03, Leu 1.02, Phe(Et) 0.97, Cys+Pen 1.48.

EXAMPLE 8

[2-D-p-Ethylphenylalanine, 8-lysine]vasopressin 100 mg of N-Benzyloxycarbonyl-S-benzylcysteinyl-D-p-ethylphenylalanyl-phenylalanyl-glutaminyl-asparaginyl-S-benzylcysteinyl-prolyl-$N^\epsilon$-p-toluenesulfonyllysyl-glycinamide was reduced with 40 ml of sodium in liquid ammonia until a blue coloration was stable for 60 seconds. This coloration was then removed by the addition of acetic acid and the solution freeze-dried. The residue was then dissolved in 0.1M HCl (10 ml), diluted with water to 200 ml, and adjusted to a pH of 7. After the addition of a $K_3Fe(CN)_6$ solution which yielded a permanent yellow coloration, this pH was maintained while stirring for 1 hour. The solution was then applied on a column of carboxylate cation-exchanger, the column washed with 0.05% acetic acid and eluted with 50% acetic acid. The product was freeze-dried, dissolved in 10 ml of water, applied on a column of silica gel modified with octadecyl chains (column dimension 50×0.9 cm), and eluted with a methanol—0.1% aqueous trifluoroacetic acid (40:60) mixture. The pertinent fractions were freeze-dried. Purity of the product was checked by thin-layer chromatography (4 solvent systems) and paper electrophoresis (2 buffers of different pH). Analysis of amino acids: Lys 1.07, Asp 1.03, Glu 0.92, Pro 0.94, Gly 1.04, Cys 1.84, Phe 1.06, Phe(Et) 0.92.

EXAMPLE 9

$N^\delta$-Glycyl-glycyl-glycyl[2-D-p-ethylphenylalanine]oxytocin

A solution of 10 mg of N-hydroxysuccinimide ester of o-nitro-benzenesulfenylglycyl-glycyl-glycine in 0.3 ml dimethylformamide was added to a solution of 4 mg of [2-D-p-ethylphenylalalanine]oxytocin in 0.3 ml of water. After stirring at ambient temperature for 2 hours, 14 mg of an additional active ester of triglycine was added and the solution alkalized to a pH of 8 by the addition of 11 μl of 1M NaOH. The reaction was followed by means of reversed-phase high-pressure liquid chromatography. After the starting compound disappeared (20 h), the solution was evaporated in a vacuum on a rotation evaporator at ambient temperature. Then, the residue was dissolved in 1 ml of methanol and 60 μl of 2.3M HCL in ether added. The solution was then allowed to stand at ambient temperature for 5 minutes and again evaporated. The residue was dispersed in 1 ml 3M acetic acid and filtered. The filtrate was diluted with 5 ml of water, applied on a column of silica gel, modified with octadecyl chains (column dimension 50×0.9 cm), and eluted under the following conditions: the mobile phase methanol—0.1% aqueous trifluoroacetic acid (40:60) for 40 min and then a linear gradient to the methanol content 60% for 20 min, flow rate 4 ml/min. The pertinent fractions were concentrated in vacuum and freeze-dried to yield 2.3 mg of product, which was chromatographically (TLC, HPLC) and electrophoretically pure. Analysis of amino acids: Asp 0.99, Glu 1.05, Pro 0.90, Gly 4.08, Cys 1.29, Ile 0.96, Leu 1.02, Phe(Et) 0.99.

EXAMPLE 10

[2-D-p-methylphenylalanine, 9-desglycinamide]deamino-6-carbaoxytocin 2.5 mg of [2-D-p-Methylphenylalanine]deamino-6-carbaoxytocin was dissolved in 50 μl of methanol and 300 μl of a 20 mM phosphate buffer of pH 7.7. Then, 2.5 mg of chymotrypsin was added and the mixture incubated at 37 degrees C. for 12 hours. The reaction was followed by means of high-performance liquid chromatography. After the starting compound disappeared, the reation mixture was applied on a column (25×0.4 cm) of silica gel modified with octadecyl chains and eluted with methanol—0.05M ammonium acetate mixture of pH 7.0 (40:60) as a mobile phase. The compound of formula (1) which proved chromatographically pure in four solvent systems used in thin-layer chromatography and in two systems in high-performance liquid chromatography, was obtained by freeze-drying in the amount of 1.6 mg. Analysis of amino acids: Asp 0.96, Glu 0.98, Pro 1.02, Hcy($C_2H_4CO_2H$) 0.93, Ile 1.03, Leu 1.03, Phe(Me) 1.05.

We claim:

1. Analog of neurohypophysial hormone which evidences inhibition properties having the formula $$\begin{array}{c} R^1 \\ | \\ R^2-C\text{————}R^5\text{————}CH_2 \\ | \qquad\qquad * \qquad\qquad\qquad | \\ R^3\text{-CH-CO-NH-CH-CO-}X^1\text{-Gln-Asn-NH-CH-CO-Pro-}X^2\text{-}X^3 \\ | \\ CH_2 \\ | \\ \text{(C}_6H_4\text{)} \\ | \\ R^4 \end{array}$$

wherein chiral amino acids are of the L-series and the aromatic amino acid in position 2, as indicated by the asterisk, is of the D-series, $R^1$ and $R^2$ being selected from the group consisting of hydrogen and a methyl group, $R^3$ being selected from the group consisting of hydrogen, an amino group or a triglycylamino group, $R^4$ being selected from the group consisting of hydrogen, a methyl group, an ethyl group and an ethoxyl group, $R^5$ being selected from the group consisting of $S-CH_2$ and $S-S$, $X^1$ being selected from the group consisting of isoleucine and phenylalanine, $X^2$ being selected from the group consisting of leucine or lysine, and $X^3$ being selected from the group consisting of a glycinamide residue and a hydroxyl group.

2. Analog in accordance with claim 1, wherein $R^1$, $R^2$, $R^3$ and $R^4$ is a hydrogen, $R^5$ is $S-CH_2$, $X^1$ is Ile, $X^2$ is Leu and $X^3$ is Gly.$NH_2$.

3. Analog in accordance with claim 1, wherein $R^1$, $R^2$ and $R^3$ is a hydrogen, $R^4$ is $OC_2H_5$, $R^5$ is $S-CH_2$, $X^1$ is Ile, $X^2$ is Leu and $X^3$ is Gly.$NH_2$.

4. Analog in accordance with claim 1, wherein $R^1$, $R^2$ and $R^3$ is a hydrogen, $R^4$ is $CH_3$, $R^5$ is $S-CH_2$, $X^1$ is Ile, $X^2$ is Leu and $X^3$ is Gly.$NH_2$.

5. Analog in accordance with claim 1, wherein $R^1$, $R^2$ and $R^3$ is a hydrogen, $R^4$ is $C_2H_5$, $R^5$ is $S-CH_2$, $X^1$ is Ile, $X^2$ is Leu and $X^3$ is Gly.$NH_2$.

6. Analog in accordance with claim 1, wherein $R^1$, $R^2$ and $R^3$ is a hydrogen, $R^4$ is $C_2H_5$, $R^5$ is $S-S$, $X^1$ is Ile, $X^2$ is Leu and $X^3$ is Gly.$NH_2$.

7. Analog in accordance with claim 1, wherein $R^1$ and $R^2$ is a hydrogen, $R^3$ is $NH_2$, $R^4$ is $C_2H_5$, $R^5$ is $S-S$, $X^1$ is Ile, $X^2$ is Leu and $X^3$ is Gly.$NH_2$.

8. Analog in accordance with claim 1, wherein $R^1$ and $R^2$ is $CH_3$, $R^3$ is $NH_2$, $R^4$ is $C_2H_5$, $R^5$ is $S-S$, $X^1$ is Ile, $X^2$ is Leu and $X^3$ is Gly.$NH_2$.

9. Analog in accordance with claim 1, wherein $R^1$ and $R^2$ is a hydrogen, $R^3$ is $NH_2$, $R^4$ is $C_2H_5$, $R^5$ is $S-S$, $X^1$ is Phe, $X^2$ is Lys and $X^3$ is Gly.$NH_2$.

10. Analog in accordance with claim 1, wherein $R^1$ and $R^2$ is a hydrogen, $R^3$ is Gly-Gly-Gly-NH, $R^4$ is $C_2H_5$, $R^5$ is $S-S$, $X^1$ is Ile, $X^2$ is Leu and $X^3$ is Gly.$NH_2$.

11. Analog in accordance with claim 1, wherein $R^1$, $R^2$ and $R^3$ is a hydrogen, $R^4$ is $CH_3$, $R^5$ is $S-CH_3$, $X^1$ is Ile, $X^2$ is Leu and $X_3$ is OH.

12. Analog of neurohypophysial hormone which evidences inhibition properties having the formula $$\begin{array}{c} R^1 \\ | \\ R^2-C\text{————}R^5\text{————}CH_2 \\ | \qquad\qquad\qquad\qquad\qquad | \\ R^3-CH-CO-NH-CH-CO-X^1-Gln-Asn-NH-CH-CO-Pro-X^2-X^3 \\ | \\ CH_2 \\ | \\ \text{(C}_6H_4\text{)} \\ | \\ R^4 \end{array}$$

wherein chiral amino acids are of the L-series and the aromatic amino acid in position 2, as indicated by the asterisk, is of the D-series, $R^1$ and $R^2$ being selected from the group consisting of hydrogen and a methyl group, $R^3$ being selected from the group consisting of hydrogen, an amino group or a triglycylamino group, $R^4$ being selected from the group consisting of a methyl group and an ethyl group, $R^5$ being selected from the group consisting of $S-CH_2$ and $S-S$, $X^1$ being selected from the group consisting of isoleucine and phenylalanine, $X^2$ being selected from the group consisting of leucine and lysine, and $X^3$ being selected from the group consisting of a glycinamide residue and a hydroxyl group.

* * * * *